United States Patent [19]

Borsanyi

[11] 4,387,734

[45] Jun. 14, 1983

[54] APPARATUS AND METHOD FOR SPONTANEOUS MENISCUS GENERATION

[75] Inventor: Alexander S. Borsanyi, Corona del Mar, Calif.

[73] Assignee: American Hospital Supply Corporation, Evanston, Ill.

[21] Appl. No.: 283,984

[22] Filed: Jul. 16, 1981

[51] Int. Cl.³ ............................................. A61M 5/14
[52] U.S. Cl. ................................. 137/206; 251/125; 222/420; 604/251
[58] Field of Search ...................... 251/125; 137/206; 222/420, 421; 604/251, 252, 253, 254, 255; 73/861.41

[56] References Cited

U.S. PATENT DOCUMENTS

| | | | |
|---|---|---|---|
| 1,269,666 | 6/1918 | Wheeler | 251/125 X |
| 2,232,029 | 2/1941 | Juchli | 222/420 |
| 3,826,137 | 7/1974 | Claski | 222/420 X |

Primary Examiner—Alan Cohan
Attorney, Agent, or Firm—Tilton, Fallon, Lungmus

[57] ABSTRACT

An apparatus and method are described for converting a continuous fluid stream into a succession of discrete fluid segments or boluses traveling independently of each other in a capillary passage, the menisci of the boluses so generated providing a clear basis for observing, accurately measuring, and controlling fluid flow. The meniscus generator is surrounded by a second fluid immiscible with the first fluid, and the wall of the capillary passage is provided with a longitudinal slit for reducing the effect of surface tension, for the spontaneous formation of boluses of the first fluid, for eliminating the effect of differential pressure on the boluses, and for maintaining separation of the boluses.

31 Claims, 12 Drawing Figures

U.S. Patent   Jun. 14, 1983   Sheet 1 of 2   4,387,734
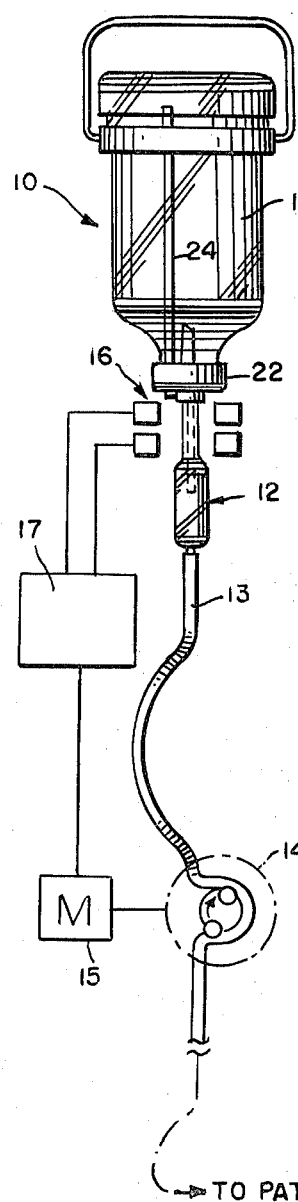
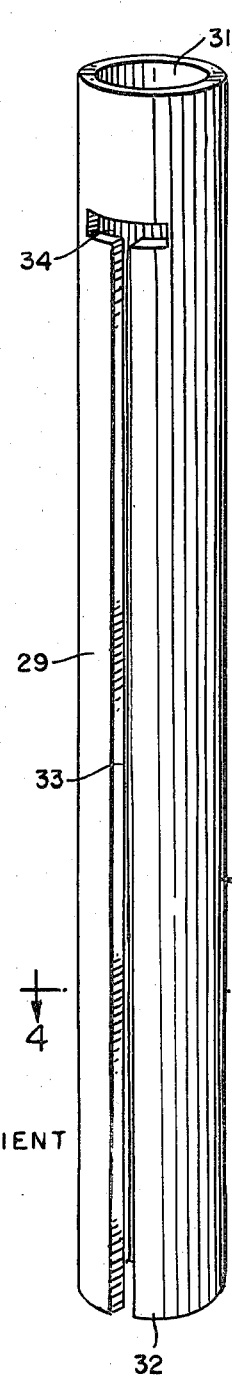
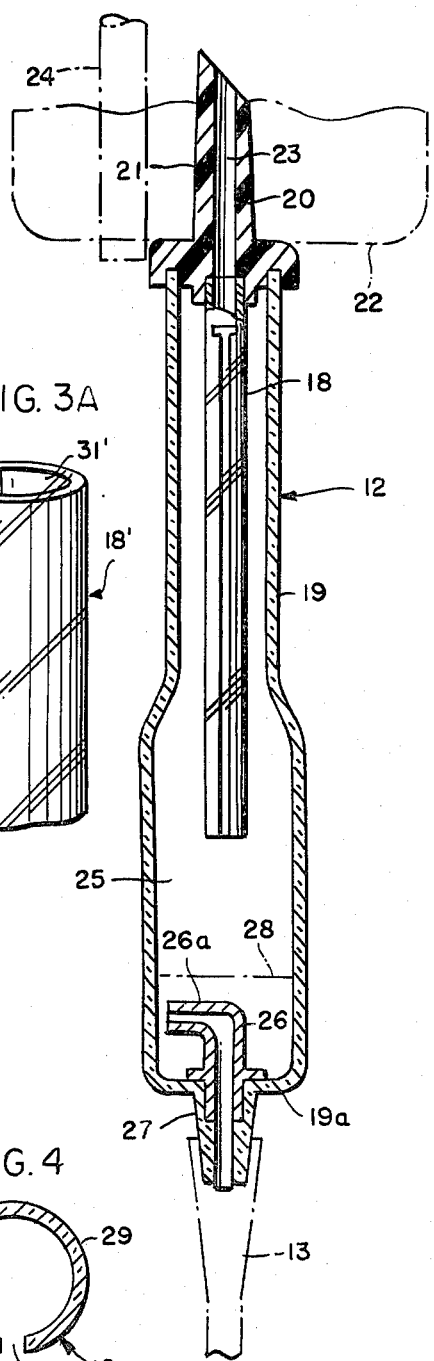
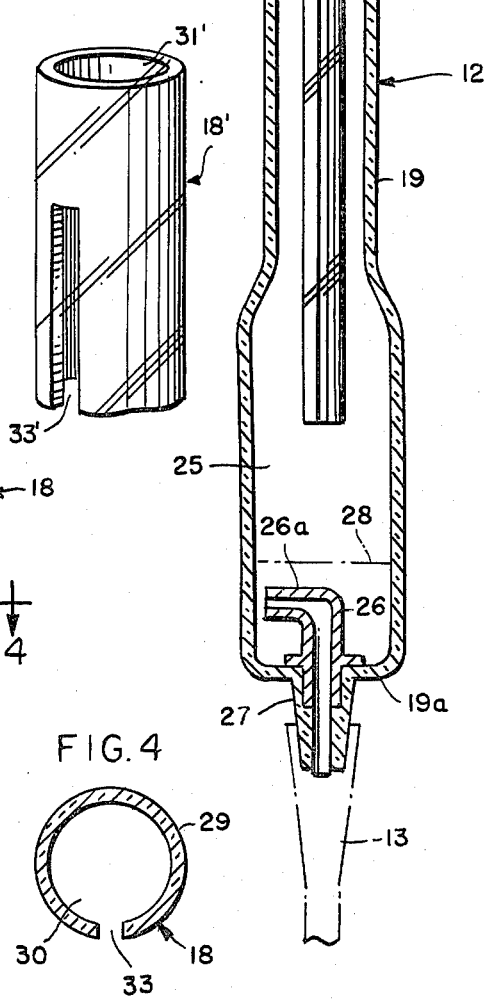
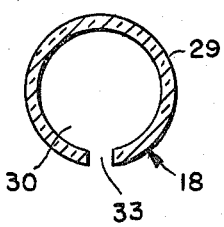

APPARATUS AND METHOD FOR SPONTANEOUS MENISCUS GENERATION

BACKGROUND AND SUMMARY

For years there has been a demand for a simple, accurate, and inexpensive device for measuring and controlling the delivery of intravenous solutions. Traditionally, IV solution flow rates have been set by timing the number of observed drops generated in a drip chamber. On the premise that drop volume is constant, and does not vary significantly from fluid to fluid, delivery rates may be readily calculated.

The problem, which is well recognized, is that drop volume is really not a constant but depends on numerous variables, with the result that the difference between actual flow rates and calculated flow rates may be substantial, conceivably as much as 30 percent or more. Since intravenous solutions frequently contain drug additives, it is apparent that variations in drop sizes, or the inability to determine accurately and quickly the precise volume of a drop, may result in substantial dosage errors.

Numerous devices have been proposed, and in certain cases marketed, for insuring greater accuracy in the delivery of parenteral fluids. In some instances, such devices have simply indicated flow rates, leaving it to the medical technician or user to make manual adjustments of a standard flow-controlling valve, whereas in other instances such devices have been designed to automatically control flow as well as to indicate flow rate. In general, such efforts have been unsatisfactory because of complexity, inaccuracy, expense, and mechanical malfunctions in use. It is apparent the malfunctioning of a flow control device might have even more serious consequences for a patient than a miscalculation of dosage in the use of the simpler and more conventional drip chamber assemblies. Consequently, there is a need for a simple, accurate control device that is reliable and inexpensive to produce.

Accordingly, it is an object of the present invention to provide a system that shares the simplicity and other advantages of the drip chamber approach without the disadvantages inherent in such an approach. Specifically, it is an object to provide a device and method for converting a continuous fluid stream into a succession of discrete fluid segments traveling through a capillary passage, in contrast to free-falling droplets passing through a drip chamber, so that the partially confined segments may be observed and accurately measured. Since the capillary passage is of established cross section, measurement of fluid segment length and frequency provides all of the information needed for an accurate determination of flow rate.

An important aspect of this invention lies in the discovery that a continuous stream of fluid introduced into one end of an upstanding capillary tube will spontaneously separate into discrete segments with observable menisci if the capillary tube is provided with a longitudinal slit that places the bore of the tube in open communication with a chamber surrounding the tube and containing a second fluid immiscible with the first. The term "fluid" is used herein to refer to both liquids and gases. Ordinarily the first fluid will be a liquid introduced into the upper end of the capillary passage and the second fluid will be a gas such as air surrounding the segment generator; however, it is conceivable that the first fluid might be a gas and the second a liquid (in which case the direction of flow would be reversed), or that both fluids might be liquids (in which case the direction of flow would depend on their relative specific gravities).

The surrounding chamber may take the form of a drip chamber with the lower end of the slit capillary tube freely suspended or supported above the bottom of that chamber, and with the upper end of the capillary tube connected to any suitable conduit means for directing liquid to the upper end of the capillary passage. As the continuous column of liquid enters the capillary tube and reaches the top of the vertically-elongated slit, air segmentation of the liquid column spontaneously occurs with each liquid segment separating from the liquid column and accelerating until the gravitational, capillary, and frictional forces reach equilibrium. Subsequently, the segment or bolus travels at a constant velocity to the open lower end of the tube. The vertical slit permits unimpeded movement of each discrete liquid segment through the capillary passage because both the leading and trailing surfaces (i.e., menisci) of each segment are subjected to the same ambient pressure; hence, the slit not only initiates liquid segmentation but also promotes the unrestrained travel of such segments to the open lower end of the tube where they are discharged as droplets into the drip chamber.

The descending segments have their lateral surfaces defined by the capillary passage and, therefore, the flow of liquid through the passage may be precisely ascertained if the length and frequency of the segments are known. Detecting means along the tube may be used in conjunction with electronic measuring means for determining and displaying flow rate based on integrated segment length per unit time.

The capillary passage would ordinarily be straight and of uniform cross section. The wall of the capillary tube or generator is preferably transparent and its inner surface must be treated or formed so that it resists wetting by the liquid passing through it. To function effectively as a segment generator, the passage should be of capillary size, falling within the broad range of about 0.5 to 5.0 millimeters in diameter with a preferred range of about 1.0 to 3.0 millimeters. The longitudinal slit may have a width within the range of 0.2 to 1.5 millimeters, preferably 0.5 to 0.9 millimeters, and the length of the capillary passage should be at least one centimeter.

It has also been found that segment generation is enhanced if there is a lateral opening, preferably a lateral enlargement of the longitudinal slit, at or adjacent the upper end of the slit. Such an enlargement or cross slit is particularly helpful where relatively high flow rate capabilities are required.

Other features, advantages, and objects of the invention will become apparent from the specification and drawings.

DRAWINGS

FIG. 1 is a somewhat schematic elevational view of a fluid administration apparatus including the segment generator assembly of this invention.

FIG. 2 is an enlarged vertical sectional view of the segment generating assembly.

FIG. 3 is a further enlarged perspective view depicting the segment generator per se.

FIG. 3A is a perspective view similar to FIG. 3 but illustrating an alternate construction of the generator's upper end portion.

FIG. 4 is a transverse sectional view taken along line 4—4 of FIG. 3.

DETAILED DESCRIPTION

Figure 5:
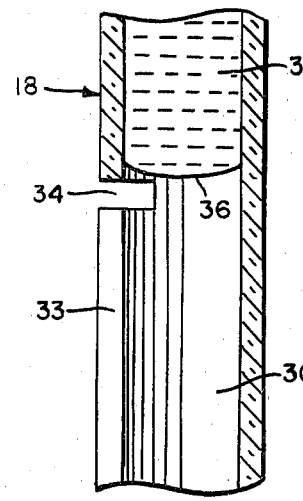
FIGS. 5-8 are fragmentary longitudinal sectional views of the capillary tube illustrating stages in the generation of a fluid segment.

For purposes of illustration, the segment or meniscus generating assembly is depicted in the drawings as part of a parenteral fluid administration apparatus generally designated by the numeral 10 in FIG. 1. While the invention is believed to have particular utility in connection with the administration of such medical fluids, it is believed apparent that the assembly has wide applicability and that it might be utilized in many systems requiring precise control over fluid delivery such as mass transfer systems, proportional fluid mixing systems, and the like.

The administration apparatus includes a conventional parenteral solution container 11 providing a reservoir for liquid flowing to the segment generating assembly 12. Tubing 13 leads from the lower end of that assembly to a suitable needle or cannula (not shown) for intravenous delivery to a patient. Pumping means 14 driven by motor 15 may be interposed along tubing 13. Sensing means 16 detects the length and frequency of the segments after they are formed in the segment generating assembly 12 and transmits signals to signal processing means 17, the latter integrating the length of the segments per unit time to establish actual flow rate or, alternatively, the sensing means 16 detects the leading surface at two fixed points prior to segment separation, and the processing means 17 integrates the elapse of time to establish the flow rate. If desired, the processing means may compare that rate with a predetermined or set flow rate and the increase or decrease the variable speed motor 15 to vary the operation of pump 14. The generation of liquid segments or boluses may thus be increased or decreased in frequency to match the desired predetermined administration rate.

The segment generating assembly 12 is shown in greater detail in FIG. 2 and comprises segment generator 18 supported within a housing 19. A connector 20 is secured to the upper end of the housing and includes a tubular spike 21 projecting through the stopper 22 of inverted bottle 11. The lumen 23 of the spike provides a conduit for the flow of a continuous stream of fluid from the reservoir (bottle) to the segment generator 18. An air inletting tube 24 admits air into the bottle as liquid drains therefrom, in accordance with conventional construction and operation of parenteral fluid administration containers.

Housing 19 may be formed of any suitable transparent material, either glass or plastic (rigid or flexible), and defines a chamber 25 that not only surrounds the sides of segment generator 18 but also extends downwardly well below the lower end of that generator. While the housing 19 has curved or cylindrical surfaces, considerable variation is possible to meet the requirements of any given application. For example, the wall of housing 19 might have opposing flattened zones for improved optical properties, or inner and outer surface portions may be non-concentric to provide visual magnification. The bottom wall 19a of the housing is apertured to receive an outlet fitting 26 for the discharge of liquid from the chamber, the fitting being provided externally with a tapered extension 27 for connection to flexible tubing 13. A typical liquid level within housing 19 is represented by line 28 in FIG. 2, such level being spaced below the lower end of generator 18 so that the interior of the housing functions as a drip chamber, i.e., allows separation of liquid and air, and visual detection of drops. In the construction shown, outlet fitting 26 is elbow-shaped, with a laterally-turned portion 26a disposed within the housing 19, to eliminate the possibility that air (or other ambient fluid) might enter the outlet by reason of splashing occasioned by the droplets of liquid discharged at substantial velocity from the lower end of generator 18 and impacting on liquid level 28.

The segment generator 18 is tubular, having a wall 29 defining an elongated and upwardly-extending capillary passage 30 of generally uniform cross sectional dimensions throughout the full length of the generator tube. The tube is open-ended, having an inlet 31 at its upper end and an outlet 32 at its lower end. The upper end portion of the generator tube 18 is secured to connector 20 so that the passage 30 of the tube is in direct open communication with the lumen 23 of connector 20 (FIG. 2). While the cross section of passage 30 would normally be made as uniform as possible throughout the length of the generator tube, some variation is possible. For example, a gradual and precisely-formed increase in cross section in a downward direction may be provided for the purpose of increasing travel time of fluid segments at high flow rates.

A longitudinal slit 33 extends substantially the full length of the tubular generator 18. Specifically, slit 33 extends through the wall 29 of the tube and continues all the way to the lower limits of that tube. The slit is shown to be generally straight and parallel to the axis of the tube; however, the primary requirement is that the slit's general direction must be longitudinal (e.g., a spiral configuration for the slit might be utilized). At or near the upper end of slit 33, tube 18 has a lateral opening in the form of cross slit 34. Ideally, the cross slit comprises a lateral enlargement at the upper end of slit 33 (as shown). While the provision of such an enlargement or cross slit is desirable in promoting fluid segmentation, and particularly for increasing the maximum frequency of such segmentation and hence the flow capability of the generator, such enlargement may be omitted, as represented in FIG. 3A. The generator tube 18' depicted in FIG. 3A is otherwise identical to tube 18 of FIG. 3.

Other variations in generator configuration and orientation are possible and might be utilized without destroying the segment-generating properties thereof. Thus, the slit-tube generator might have a helical configuration (with the axis of the helix extending generally vertically), the generator might be tipped to a limited extent so that while it is no longer vertical it nevertheless generates fluid segments under the influence of gravity, the bore and/or cross sectional outline of the generator might be non-circular, and more than one slit 33 might be provided in the generator tube to allow, for example, observation of the menisci even if the tubular wall were formed of opaque material.

Figure 6:
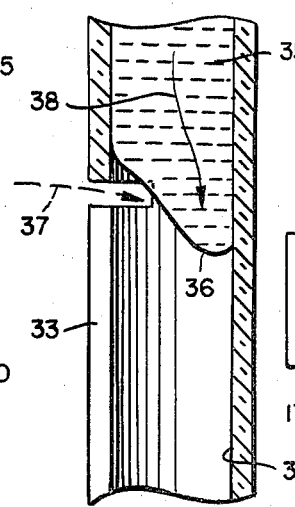
Figure 8:
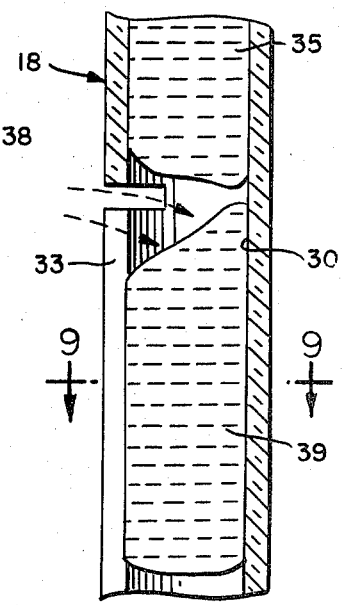
Figure 9:
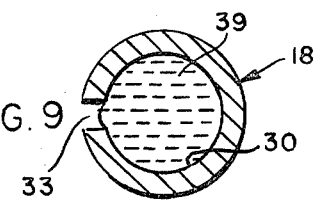
FIG. 9 is a sectional view taken along line 9—9 of FIG. 8.

FIGS. 5–10 schematically depict successive stages in the formation of a fluid segment or bolus within generator tube 18. A column of liquid 35 enters the upper end of the generator tube from connector 20 and reservoir 11. As the lower or leading meniscus 36 of the column reaches enlargement 34 of slit 33, air (or other surrounding fluid in chamber 25) enters passage 30 to deform the lower end of the column as shown in FIG. 6. The entry of air is represented by dashed arrow 37 and the altered path of liquid flow is indicated by arrow 38. Liquid continues to flow downwardly into the zone below the upper end 34 of slit 33 (FIG. 7), and finally when the force of gravity exceeds the surface tension of the liquid, a bolus or segment 39 detaches from the column immediately below the upper end of the slit (FIG. 8). Because of slit 33, air or other ambient fluid is free to enter passage 30 above the bolus and exit laterally from the passage beneath the descending bolus. Consequently, no pressure differential exists; the same ambient pressure exists both above and below the descending bolus. The bolus accelerates downwardly, ultimately reaching the tube's lower end where it forms a droplet that releases into drip chamber 25.

Figure 10:
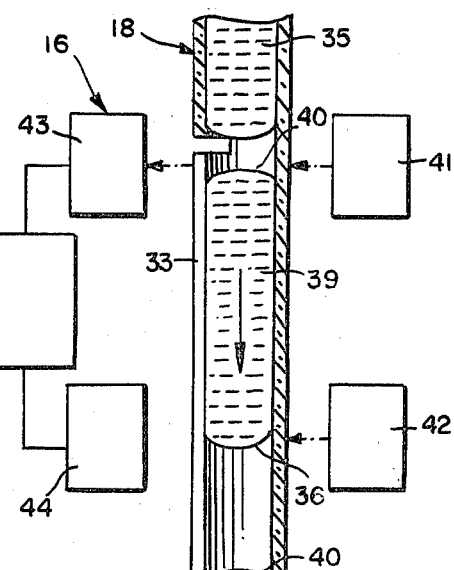
FIG. 10 is a longitudinal sectional view showing one segment accelerating immediately after formation thereof, another segment moving towards the lower end of the tube, and a further segment forming a droplet at the tube's lower end.
Figure 7:
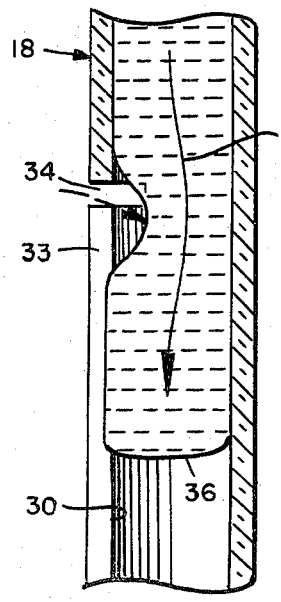

Since the capillary passage 30 defines the cross sectional dimensions of each segment or bolus 39, and since the cross sectional dimensions of passage 30 are uniform for the full length of slit 33, or at least for the portion of the generator tube along which segment detection and measurement occurs, the volume of each liquid segment is proportional to its length. By determining segment length—that is, the distance between the lower or leading meniscus 36 and the upper or trailing meniscus 40 (FIG. 10),—and also determining the frequency or segment (or meniscus) formation, flow rate may be readily computed. Segment length and formation frequency may be detected by sensing means 16 which in FIG. 10 is diagramatically represented by beam emitters 41 and 42 and receivers or sensors 43 and 44. The beam from emitter 41 impinges on sensor 43 as soon as upper meniscus 40 is formed and before the lower meniscus of the fluid column 35 has advanced sufficiently to interrupt that beam. Segment length may be established by emitter 42 and sensor 44, positioned for detecting and locating lower meniscus 36 of the segment 39 at the instant the upper meniscus has developed. The emitters 41 and 42 (also 41' and 42') and receivers 43 and 44 (also 43' and 44') could be arranged in an array to facilitate measurement of the varying length, moving segments.

Figure 11:
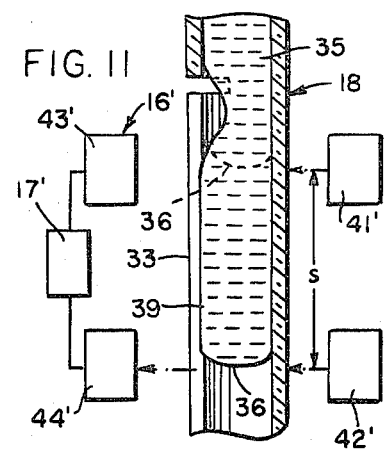
FIG. 11 is a fragmentary longitudinal sectional view similar to FIG. 10 but illustrating a variation of the detecting and measuring system.

Another method of flow rate measurement may be based upon measurement of the velocity of the leading or lower meniscus of the segment prior to separation, as indicated in FIG. 11. The two sensors 43' and 44', along with processing means 17', measure the time (t) required for the leading meniscus 36 to travel from the upper sensor to the lower one. The velocity of the leading meniscus may be calculated from the formula $V = s/t$, where s is the distance between the upper and lower sensors, which could be constant. Since the cross section of the development segment 39 is constant as defined by the cross sectional dimensions of the slit capillary generator, the flow rate is equal to the velocity multiplied by the cross sectional area of the fluid segment.

Each of the methods of FIGS. 10 and 11 may be used continuously, measuring successive boluses, or may be used intermittently to sample the flow at predetermined intervals. It is also believed apparent that small distortions or assymetry of the menisci may be factored into the software of the computer-controller.

The fluid stream could be a homogeneous fluid or a two phase liquid-gas mixture. The meniscus generator would separate the gas phase at the cross slit 34 and generate a discrete segment of liquid in the slit section of tube 29 from the incoming liquid phase. A partially-formed bolus would remain stationary at the cross slit until sufficient volume were developed to cause the bolus to break away. Measurement of the volume of such a discrete fluid segment could then be made as already described. It is believed apparent that instead of a gas-liquid mixture, a combination of two or more immiscible liquids might be used, or a combination of immiscible liquids and gases. Any combination of such fluid streams could be constant, fluctuating, or intermittent.

Since segmentation necessarily involves the generation of menisci, and since the detecting means is directed to the menisci so developed, tube 18 may be properly regarded as a menisci generator as well as a segment generator. As mentioned, passage 30 is shown to be generally cylindrical although other cross sectional configurations might be provided. It is important that the cross sectional dimensions of such passage be small enough to insure that the full cross sectional area will be occupied by a segment as it forms and descends. While such dimensions would vary depending on the fluid involved, a maximum size for a cylindrical passage is believed to be about 5.0 millimeters in diameter. The minimum diameter depends on a number of factors, including slit widths, fluid characteristics, and the manufacturing capability of forming small diameter passages of uniform cross section, but a practical minimum is believed to be about 0.5 millimeters. A preferred range is considered to be about 1.0 to 3.0 millimeters in diameter. The length of the tube is not critical except that it must be long enough to permit the formation of at least one segment adjacent the upper end of the slit; thus, the minimum length for the slitted portion of the tubular generator is believed to be about one centimeter, with lengths over 2 centimeters being preferred. The slit must not be so narrow that it prevents entry of ambient fluid (e.g., air) into the passage of the tubular generator, nor so large that it permits lateral escape of fluid segments or prevents such segments from conforming to the interior cross section of the tube. In general, the slit width should fall within the range of 0.2 to 1.5 millimeters, the preferred range being 0.5 to 0.9 millimeters.

The surface of passage 30 should be hydrophobic or, more broadly, should be incapable of being wetted by the fluid undergoing segmentation within the capillary passage. For aqueous fluids such as conventional parenteral solutions, the generator tube may be formed from any of a variety of polymeric materials such as acrylic and styrene polymers by properly compounding the resin with hydrophobic additives such as paraffin, silicone compounds, etc. Non-hydrophobic materials may also be used if they are surface treated or lined to impart non-wettability to the surface of the passage such as, for example, by dip coating, spin coating, or other known techniques for applying coating materials. A suitable silicone fluid, such as Dow Corning 200, may be used as a treating agent when the generator tube is formed of glass or a polymeric composition that is not inherently non-wetting. Linings of Teflon or other hydrophobic materials may also be used to achieve the same purpose.

While in the foregoing I have disclosed embodiments of the invention in considerable detail for purposes of illustration, it will be understood by those skilled in the art that many of these details may be varied without departing from the spirit and scope of the invention.

I claim:

1. An apparatus for converting a stream of fluid into a succession of discrete fluid segments with leading and trailing menisci, comprising a segment generator having a wall defining an elongated and downwardly-extending capillary passage having an inlet at one end and an outlet at the other end thereof, conduit means for conducting a generally continuous stream of fluid to said inlet, said wall of said generator having at least one longitudinally-extending slit therethrough, said slit having one end disposed adjacent said inlet for initiating the generation of fluid segments and extending along said capillary passage to said outlet, said capillary passage being provided with a non-wettable surface.

2. The apparatus of claim 1 in which said capillary passage is of generally uniform cross section along the full length of said slit.

3. The apparatus of claim 1 or 2 in which said capillary passage is generally straight and generally circular in cross sectional outline.

4. The apparatus of claim 3 in which said capillary passage has a diameter within the range of about 0.5 to 5.0 millimeters.

5. The apparatus of claim 4 in which said diameter is within the range of 1.0 to 3.0 millimeters.

6. The apparatus of claim 1 or 2 in which said slit has a width within the range of 0.2 to 1.5 millimeters.

7. The apparatus of claim 6 in which said width falls within the range of 0.5 to 0.9 millimeters.

8. The apparatus of claim 1 in which means are provided for detecting the menisci of fluid segments traveling downwardly within said passage.

9. The apparatus of claim 8 in which said means also includes means for measuring the length and frequency of formation of discrete fluid segments within said capillary passage.

10. The apparatus of claim 8 in which said means also includes means for measuring the velocity of the menisci of said fluid segments immediately after the leading edge is formed and prior to separation of such segments from a fluid column.

11. The apparatus of claim 1 in which said wall of said segment generator is transparent.

12. An apparatus for converting a stream of fluid into a succession of discrete fluid segments, comprising a generally tubular segment generator having a wall defining an elongated, substantially cylindrical, and generally vertical capillary passage having an inlet at one end and an outlet at the other end thereof, conduit means for conducting a stream of fluid to said inlet, said wall of said tubular generator having a longitudinally-extending slit therethrough communicating with said capillary passage, said slit having one end disposed adjacent said inlet for initiating the generation of fluid segments and extending along said capillary passage to said outlet, said capillary passage having a diameter within the range of about 0.5 to 5.0 millimeters, and said slit having a width within the range of about 0.2 to 1.5 millimeters, said capillary passage being provided with a non-wettable surface.

13. The apparatus of claim 12 in which said capillary passage has a diameter within the range of 1.0 to 3.0 millimeters.

14. The apparatus of claim 12 in which said slit has a width within the range of 0.5 to 0.9 millimeters.

15. The apparatus of claim 12 in which said tubular generator has a length of at least one centimeter.

16. The apparatus of claim 10 in which means are provided for detecting menisci of fluid segments formed or forming in said capillary passage.

17. The apparatus of claim 10 in which said tubular generator is formed of transparent material.

18. An apparatus for converting a stream of liquid into a succession of liquid segments having detectable upper and lower menisci, comprising a segment generator having a wall defining a downwardly extending capillary passage having an inlet at its upper end and an outlet at its lower end, conduit means for conducting a substantially continuous stream of liquid to said inlet, means defining a gas chamber about said generator, said wall of said generator having a longitudinal slit therethrough and communicating with both said capillary passage and said gas chamber, said slit having an upper end disposed adjacent said inlet for spontaneous meniscus generation thereat and extending downwardly along said capillary passage to said outlet, said capillary passage being provided with a nonwettable surface.

19. The apparatus of claim 17 in which said capillary passage is of substantially uniform cross section throughout the full length of said slit.

20. The apparatus of claim 19 in which said cross section is generally circular.

21. The apparatus of claim 20 in which said capillary passage has a diameter within the range of about 0.5 to 5.0 millimeters.

22. The apparatus of claim 21 in which said diameter falls within the range of about 1.0 to 3.0 millimeters.

23. The apparatus of claim 18 in which said slit has a width within the range of 0.2 to 1.5 millimeters.

24. The apparatus of claim 23 in which said slit has a width within the range of about 0.5 to 0.9 millimeters.

25. The apparatus of claim 18 in which said capillary passage has a length of at least one centimeter.

26. The apparatus of claim 1, 12, or 18 in which said wall of said generator is provided with a cross slit adjacent the inlet end of said capillary passage.

27. The apparatus of claim 26 in which said cross slit comprises a lateral enlargement at one end of said longitudinal slit.

28. The apparatus of claim 18 in which said generator is formed of transparent material.

29. The apparatus of claim 28 in which means are provided for detecting menisci of fluid segments formed in said capillary passage.

30. A method for converting a stream of liquid into a succession of liquid segments with leading and trailing menisci, comprising the steps of supporting an elongated capillary tube in a generally vertical direction within a gas-containing chamber, said tube having a capillary passage with a non-wettable surface and having a longitudinal slit communicating with both said passage and said chamber, said tube also having an inlet at the upper end thereof and an outlet at the lower end thereof, conducting a continuous column of liquid to the inlet of said tube, and allowing said liquid to descend in said tube under the influence of gravity while spontaneously inducting gas into said capillary passage through said slit adjacent the inlet of said tube, thereby causing said column to separate into a succession of discrete liquid segments having leading and trailing menisci.

31. The method of claim 30 in which there is the further step of detecting menisci of said segments within said tube.

* * * * *